(12) United States Patent
Maschino et al.

(10) Patent No.: US 7,499,752 B2
(45) Date of Patent: Mar. 3, 2009

(54) SELECTIVE NERVE STIMULATION FOR THE TREATMENT OF EATING DISORDERS

(75) Inventors: Steven E. Maschino, Seabrook, TX (US); William Buras, Friendswood, TX (US); Stephen Brannan, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 613 days.

(21) Appl. No.: 11/192,594

(22) Filed: Jul. 29, 2005

(65) Prior Publication Data
US 2007/0027498 A1 Feb. 1, 2007

(51) Int. Cl.
*A61N 1/00* (2006.01)
(52) U.S. Cl. ...................................... 607/40
(58) Field of Classification Search ............... 607/40, 607/900; 604/500; 600/544, 409
See application file for complete search history.

(56) References Cited

U.S. PATENT DOCUMENTS

| | | | |
|---|---|---|---|
| 3,796,221 A | 3/1974 | Hagfors | |
| 4,119,618 A | 10/1978 | Said | |
| 4,431,000 A | 2/1984 | Butler et al. | |
| 4,556,064 A | 12/1985 | Pomeranz et al. | |
| 4,702,254 A | 10/1987 | Zabara | |
| 4,745,923 A | 5/1988 | Winstrom | |
| 4,867,164 A | 9/1989 | Zabara | |
| 5,025,807 A | 6/1991 | Zabara | |
| 5,269,303 A | 12/1993 | Wernicke et al. | |
| 5,299,569 A | 4/1994 | Wernicke et al. | |
| 5,311,876 A | 5/1994 | Olsen et al. | |
| 5,330,515 A | 7/1994 | Rutecki et al. | |
| 5,465,711 A | 11/1995 | Moll et al. | |
| 5,540,734 A | 7/1996 | Zabara | |
| 5,611,350 A | 3/1997 | John | |
| 5,683,422 A | 11/1997 | Rise et al. | |
| 5,716,377 A | 2/1998 | Rise et al. | |
| 5,769,778 A | 6/1998 | Abrams et al. | |
| 5,782,798 A * | 7/1998 | Rise ........................... 604/500 | |
| 5,792,186 A | 8/1998 | Rise | |

(Continued)

FOREIGN PATENT DOCUMENTS

WO 03085546 10/2003

(Continued)

OTHER PUBLICATIONS

Andrews, P.L.R. et al, "A Protective Role for Vagal Afferents: An Hypothesis," Neuroanatomy and Physiology of Abdominal Vagal Afferents, Sue Ritter et al, eds., CRC Press, New York, NY, 1992, pp. 281-298.

(Continued)

*Primary Examiner*—George Manuel
(74) *Attorney, Agent, or Firm*—Conley Rose, P.C.; Timothy L. Scott (57) ABSTRACT

A method and apparatus for treating persons suffering from an eating disorder includes direct or indirect stimulation of selected areas of the brain associated with a symptom of the eating disorder. The stimulation regimen is programmable to enable physician optimization of stimulation signal parameters to ameliorate at least one symptom of bulimia or another eating disorder. Certain embodiments employ deep brain stimulation and/or sensing together with cranial nerve stimulation and/or sensing.

24 Claims, 5 Drawing Sheets

U.S. PATENT DOCUMENTS

| | | | |
|---|---|---|---|
| 5,800,474 | A | 9/1998 | Benavid et al. |
| 5,833,709 | A | 11/1998 | Rise et al. |
| 5,899,922 | A | 5/1999 | Loos |
| 5,941,906 | A | 8/1999 | Barreras, Sr. et al. |
| 5,978,702 | A | 11/1999 | Ward et al. |
| 5,995,868 | A | 11/1999 | Osorio et al. |
| 6,016,449 | A | 1/2000 | Fischell et al. |
| 6,018,682 | A | 1/2000 | Rise |
| 6,061,593 | A | 5/2000 | Fischell et al. |
| 6,081,744 | A | 6/2000 | Loos |
| 6,104,956 | A | 8/2000 | Naritoku et al. |
| 6,109,269 | A | 8/2000 | Rise et al. |
| 6,128,538 | A | 10/2000 | Fischell et al. |
| 6,129,685 | A | 10/2000 | Howard |
| 6,132,361 | A | 10/2000 | Epstein et al. |
| 6,167,311 | A | 12/2000 | Rezai |
| 6,176,242 | B1 | 1/2001 | Rise |
| 6,205,359 | B1 | 3/2001 | Boveja |
| 6,248,080 | B1 | 6/2001 | Miesel et al. |
| 6,253,109 | B1 | 6/2001 | Gielen |
| 6,304,775 | B1 | 10/2001 | Lasemidis et al. |
| 6,319,241 | B1 | 11/2001 | King et al. |
| 6,337,997 | B1 | 1/2002 | Rise |
| 6,339,725 | B1 | 1/2002 | Naritoku et al. |
| 6,341,236 | B1 | 1/2002 | Osorio et al. |
| 6,353,762 | B1 | 3/2002 | Baudino et al. |
| 6,356,784 | B1 | 3/2002 | Lozano et al. |
| 6,356,788 | B2 | 3/2002 | Boveja |
| 6,360,122 | B1 | 3/2002 | Fischell et al. |
| 6,366,814 | B1 | 4/2002 | Boveja |
| 6,418,344 | B1 | 7/2002 | Rezai |
| 6,425,852 | B1 | 7/2002 | Epstein et al. |
| 6,449,507 | B1 | 9/2002 | Hill et al. |
| 6,459,936 | B2 | 10/2002 | Fischell et al. |
| 6,463,328 | B1 | 10/2002 | John |
| 6,466,822 | B1 | 10/2002 | Pless |
| 6,473,639 | B1 | 10/2002 | Fischell et al. |
| 6,480,743 | B1 | 11/2002 | Kirpatrick et al. |
| 6,529,774 | B1 | 3/2003 | Greene |
| 6,532,388 | B1 | 3/2003 | Hill et al. |
| 6,549,804 | B1 | 4/2003 | Osorio et al. |
| 6,556,868 | B2 | 4/2003 | Naritoku et al. |
| 6,560,486 | B1 | 5/2003 | Osorio et al. |
| 6,564,102 | B1 | 5/2003 | Boveja |
| 6,587,727 | B2 | 7/2003 | Osorio et al. |
| 6,591,138 | B1 | 7/2003 | Fischell et al. |
| 6,594,524 | B2 | 7/2003 | Esteller et al. |
| 6,609,030 | B1 | 8/2003 | Rezai et al. |
| 6,622,038 | B2 | 9/2003 | Barrett et al. |
| 6,622,047 | B2 | 9/2003 | Barrett et al. |
| 6,647,296 | B2 | 11/2003 | Fischell et al. |
| 6,671,555 | B2 | 12/2003 | Gielen et al. |
| 6,671,556 | B2 | 12/2003 | Osorio et al. |
| 6,690,974 | B2 | 2/2004 | Archer et al. |
| 6,708,064 | B2 | 3/2004 | Rezai |
| 6,721,603 | B2 | 4/2004 | Zabara et al. |
| 6,735,475 | B1 | 5/2004 | Whitehurst et al. |
| 6,760,626 | B1 | 7/2004 | Boveja |
| 6,788,975 | B1 | 9/2004 | Whitehurst et al. |
| 6,819,956 | B2 | 11/2004 | DiLorenzo |
| 6,819,958 | B2 | 11/2004 | Weiner et al. |
| 6,920,357 | B2 | 7/2005 | Osorio et al. |
| 6,944,501 | B1 | 9/2005 | Pless |
| 6,961,618 | B2 | 11/2005 | Osorio et al. |
| 7,006,872 | B2 | 2/2006 | Gielen et al. |
| 7,050,856 | B2 | 5/2006 | Sypulkowski |
| 7,054,686 | B2 | 5/2006 | MacDonald |
| 2002/0099412 | A1 | 7/2002 | Fischell et al. |
| 2002/0151939 | A1 | 10/2002 | Rezai |
| 2003/0181954 | A1 | 9/2003 | Rezai |
| 2004/0153129 | A1 | 8/2004 | Pless et al. |
| 2004/0172089 | A1 | 9/2004 | Whitehurst et al. |
| 2004/0172091 | A1 | 9/2004 | Rezai |
| 2004/0263172 | A1 | 12/2004 | Gray et al. |
| 2005/0004621 | A1 | 1/2005 | Boveja et al. |
| 2005/0021103 | A1 | 1/2005 | DiLorenzo |
| 2005/0021104 | A1 | 1/2005 | DiLorenzo |
| 2005/0049655 | A1 | 3/2005 | Boveja et al. |
| 2005/0065574 | A1 | 3/2005 | Rezai |
| 2005/0119703 | A1 | 6/2005 | DiLorenzo |
| 2005/0143786 | A1 | 6/2005 | Boveja et al. |
| 2005/0154425 | A1 | 7/2005 | Boveja et al. |
| 2005/0165458 | A1 | 7/2005 | Boveja et al. |
| 2005/0187590 | A1 | 8/2005 | Boveja et al. |
| 2005/0283200 | A1 | 12/2005 | Rezai et al. |
| 2005/0283201 | A1 | 12/2005 | Machado et al. |
| 2005/0288760 | A1 | 12/2005 | Machado et al. |
| 2006/0058627 | A1* | 3/2006 | Flaherty et al. ............. 600/409 |
| 2006/0079936 | A1 | 4/2006 | Boveja |

FOREIGN PATENT DOCUMENTS

| | | |
|---|---|---|
| WO | 2004000413 A2 | 12/2003 |
| WO | 2004036377 A2 | 4/2004 |
| WO | 2004112894 A1 | 12/2004 |
| WO | 2005028026 A1 | 3/2005 |
| WO | 2005065768 A1 | 7/2005 |

OTHER PUBLICATIONS

Bachman, D.S, et al., "Effects of Vagal Volleys and Serotonin on Units of Cingulate Cortex in Monkeys," Brain Research, 130, (1977), pp. 253-269.

Clark, K.B., et al., "Enhanced Recognition Memory Following Vagus Nerve Stimulation In Human Subjects," Nature Neuroscience, vol. 2, No. 1, Jan. 1999, pp. 94-98.

Clark, K.B., et al., "Posttraining Electrical Stimulation Of Vagal Afferents With Concomitant Vagal Efferetn Inactivation Enhances Memory Storage Processes In The Rat," Neurobiology Of Learning And Memory 70, Article No. NL983863, (1998) pp. 364-373.

Devous, Sr., Michael D. et al., "Effects Of Vagus Nerve Stimulation On Regional Cerebral Blood Flow In Treatment-Resistant Depression," National Institute Of Mental Health 42nd Annual NCDEU Meeting, Poster Abstracts, Session II-19, 1 page. Found at: http://www.nimh.nih.gov/ncdeu/abstracts2002/ncdeu2019.cfm.

Dodrill, Carl B. et al., "Effects Of Vagal Nerve Stimulation On Cognition And Quality Of Life In Epilepsy," Epilepsy & Behavior, vol. 2, 2001, pp. 46-53.

Elger, Gerda et al., "Vagus Nerve Stimulation Is Associated With Mood Improvements In Epilepsy Patients," Epilepsy Research, No. 42, 2000, pp. 203-210.

Grundy, David, et al.., "Sensory Afferents From The Gastrointestinal Tract," Handbook of Physiology, John G. Forte et al, eds., American Physiology Society, Bethesda, Md., 1989, pp. 593-619.

Hallowitz, R.A., et al., "Effects of Vagal Volleys on Units of Intralaminar and Juxtalaminar Thalamic Nuclei in Monkeys," Brain Research, 130, (1977), pp. 271-286.

Henry, Thomas R., "Therapeutic Mechanisms Of Vagus Nerve Stimulation," Neurology, vol. 59, Suppl. 4, Sep. 2002, pp. S3-S14.

Koo, Betty, "EEG Changes With Vagus Nerve Stimulation," Journal Of Clinical Neurophysiology, vol. 18, No. 5, (Sep. 2001), pp. 434-441.

Leibowitz, Sarah F., "Eating Disorders and Obesity, A Comprehensive Handbook", Brownell and Fairburn, Ed., The Guilford Press, 1995, pp. 3-7.

Liebman, Kenneth M. et al., "Improvement In Cognitive Function After Vagal Nerve Stimulator Implantation," No. 3.080, Epilepsia, vol. 39, Suppl. 6, 1998, p. 93.

Ritter, R.C. et al., "Participation Of Vagal Sensory Neurons In Putative Satiety Signals From The Upper Gastrointestinal Tract," Neuroanatomy and Physiology of Abdominal Vagal Afferents, Sue Ritter et al, eds., CRC Press, 1992, pp. 222-244.

Rogers, R.C. et al., "Central Regulation Of Brainstem Gastric Vago-Vagal Control Circuits," Neuroanatomy and Physiology of Abdominal Vagal Afferents, Sue Ritter et al, eds., CRC Press, New York, NY, 1992, pp. 100-129.

Rush, A. John et al., "Continuing Benefit Of VNS Therapy Over 2 Years For Treatment-Resistant Depression," 43rd Annual New Clinical Drug Evaluation Unit Meeting, Boca Raton, Florida, May 27-30, 2003, 1 page.

Sackeim, Harold A. et al., "The Effects Of Vagus Nerve Stimulation On Cognitive Performance In Patients With Treatment-Resistant Depression," Neuropsychiatry, Neuropsychology, And Behavioral Neurology, vol. 14, No. 1, Jan. 2001, pp. 53-62.

Sheikh, Sohail et al., "Effects Of Vagus Nerve Stimulation Therapy On Brain Metabolism In Severe, Chronic Treatment-Resistant Depression: One-Year Outcome," 58th Annual Scientific Convention Of The Society Of Biological Psychiatry, San Francisco, California, May 15-17, 2003, 1 page.

Sjogren, Magnus et al., "Cognitive Effects Of VNS Therapy In Patients With Alzheimer's Deisease—Results Of A One-Year Clinical Trial," 58th Annual Scientific Convention Of The Society Of Biological Psychiatry, San Francisco, California, May 15-17, 2003, 1 page.

Terry, R.S., et al., "The Implantable Neurocybernetic Prosthesis System," Pacing and Clinical Electrophysiology, vol. 14, No. 1, (Jan. 1991), pp. 86-93.

Theodore, William H. et al., "Brain Stimulation For Epilepsy," The Lancet Neurology, vol. 3, Feb. 2004, pp. 111-118.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

Zabara, J., et al., "Inhibition of Experimental Seizures in Canines by Repetitive Vagal Stimulation," Epilepsia, 33(6), (1992), pp. 1005-1012.

* cited by examiner

SELECTIVE NERVE STIMULATION FOR THE TREATMENT OF EATING DISORDERS

BACKGROUND OF THE INVENTION

1. Field of the Invention

The present invention generally relates to methods and apparatus for stimulating certain areas of the brain to treat eating disorders by modulation of electrical activity of neural tissue in the selected area of the brain.

2. Description of Related Art

When a person's eating behavior is disordered to such an extent that the individual's physical health is detrimentally affected, the condition is termed an eating disorder. The most familiar types of eating disorders are bulimia nervosa and anorexia nervosa. Bulimia nervosa ("bulimia") is an eating disorder in which an individual experiences recurrent episodes of insatiable craving for food often resulting in episodes of binge eating followed by inappropriate compensatory behavior to prevent weight gain. The inappropriate compensatory behavior typically includes self-induced vomiting, fasting, excessive exercise, and use of laxatives and diuretics. People suffering from bulimia commonly engage in binge eating and inappropriate compensatory behavior an average of two times a week for a period of three or more months. It has been reported that as many as 17% of college-age women engage in bulimic behaviors, although their weight is usually normal or slightly above. Anorexia nervosa is characterized by voluntary starvation which may be combined with exercise stress. An anorexic individual maintains a body weight that is below a minimally normal level for age and height. Binge eating, without compensatory purging behavior, is also a type of eating disorder characterized by consuming large quantities of food, or eating inappropriate food in secret, and weight gain.

Eating disorders have both physical and psychological components, and it has been said that eating disorders are not about food, but food is the tool that people with eating disorders abuse. Severe medical complications can develop as a consequence of an eating disorder. An eating disorder may be mild in one person and severe or even life threatening in another. Typically, an affected individual will attempt to hide his or her abnormal behavior from others, and may reject diagnosis of an eating disorder or avoid treatment.

In the human body, food intake is controlled by a complex interaction of internal and external stimuli. It is known that the vagus nerve plays a role in mediating afferent information from the stomach to the satiety centers of the brain. U.S. Pat. No. 5,188,104 (Cyberonics, Inc.) and U.S. Pat. No. 5,263,480 (Cyberonics, Inc.) disclose methods of treating eating disorders, including bulimia, that include sensing the quantity of food consumed by the patient in a predetermined period of time, and, if the consumption exceeds a predetermined level in that time period, applying a stimulating signal to the patient's vagus nerve. The output signal parameters of the neurostimulator's stimulus generator are programmed to stimulate vagal activity in such a way as to induce a sensation of fullness of the patient's stomach, upon sensing an excessive level of food consumption (i.e., exceeding the predetermined level in the selected time interval, by integrating the number of swallows of food over that interval).

U.S. Pat. No. 5,540,734 (Cyberonics, Inc.) discloses that treatment, control or prevention of several medical, psychiatric or neurological disorders may be accomplished by application of modulating electric signals to one or both of a patient's trigeminal and glossopharyngeal nerves. Among the treatable disorders are eating disorders including anorexia nervosa, bulimia and compulsive overeating.

U.S. Pat. No. 5,782,798 (Medtronic, Inc.) reports that the neural circuitry of the brain that controls eating and satiety includes neurons in the lateral hypothalamus (feeding) and the ventral medial hypothalamus (satiety). Certain techniques using drugs and electrical stimulation for treating an eating disorder by means of an implantable signal generator and electrode and an implantable pump and catheter are described. The catheter is surgically implanted in the brain to infuse drugs and the electrode is implanted in the brain to provide electrical stimulation. Stimulation sites in the brain include the lateral hypothalamus, the paraventricular nucleus and the ventral medial hypothalamus.

U.S. Patent Application Publication No. 2005/0027284 (Advanced Neuromodulation Systems, Inc.) proposes alleviation or modulation of mood and/or anxiety disorders by stimulation of subcallosal areas of the brain, such as subgenual cingulate area, subcallosal gyrus area, ventral/medial prefrontal cortex area, ventral/medial white matter, Brodmann area 24, Brodmann area 25, and/or Brodmann area 10.

New ways to treat patients suffering from severe or life threatening eating disorders that are not sufficiently responsive to conventional therapies are needed.

SUMMARY OF THE INVENTION

The inventors propose that selective deep brain stimulation is effective for treating bulimia and other eating disorders, particularly when certain areas or regions of the brain are selectively stimulated. The areas of the brain selected for treatment are associated with symptoms of bulimia and other eating disorders. More specifically, the preferred methods comprise direct or indirect stimulation of the insula, subcallosal area, cingulate, thalamus, prefrontal cerebral cortex, brain stem, cerebellum, and white matter tracts leading to an aforementioned area of the brain.

Accordingly, certain embodiments of the present invention provide a deep brain stimulation (DBS) method for treating a patient suffering from a serious eating disorder, the method comprising applying a first therapeutic stimulation signal to a first stimulator that is coupled to a predetermined stimulation site comprising a volume of neural tissue in an area of the individual's brain chosen from the group consisting of insula, subcallosal area, cingulate, thalamus, prefrontal cerebral cortex, brain stem, cerebellum, and white matter tracts leading to an aforementioned area, wherein the first stimulation signal causes modulation of the neuronal activity of the neural tissue, and the modulation of neuronal activity alleviates a symptom of the eating disorder. In certain embodiments the first stimulator comprises an electrode and the first therapeutic stimulation signal comprises a first predetermined electrical signal, and the method includes coupling the electrode to the selected area of the individual's brain; and applying the first predetermined electrical signal to the electrode such that the neuronal activity of the neural tissue is modified, wherein such modification of neuronal activity alleviates a symptom of the eating disorder.

In certain of the foregoing embodiments, the first therapeutic stimulation signal comprises an acute stimulation component and a chronic stimulation component, wherein each of the components comprises a set of electrical parameters (current, pulse width, frequency), on/off times and duration of stimulation. In some embodiments the acute stimulation component comprises a higher intensity level of stimulation and shorter duration than the chronic stimulation component. Higher intensity level stimulation comprises higher electrical parameters, on/off times and duration. In some embodiments the acute stimulation component includes a duration of one to six months.

In certain of the above-described embodiments, the method also includes cranial nerve stimulation. In some embodiments, this method includes (a) coupling the first stimulator to an area of the individual's brain selected from the group consisting of insula, subcallosal area, cingulate, thalamus, prefrontal cerebral cortex, brain stem, cerebellum, and white matter tracts leading to an aforementioned area; (b) coupling a second stimulator to a cranial nerve of the individual; (c) applying the first predetermined stimulatory signal to the first stimulator; and (d) applying a second predetermined stimulatory signal to the second stimulator, wherein the application of the first and second signals causes modulation of neuronal activity of the neural tissue to ameliorate the eating disorder. In certain of these embodiments, the second therapeutic stimulation signal comprises a second acute stimulation component and a second chronic stimulation component. In some embodiments the second acute stimulation component comprises a higher intensity level of stimulation and shorter duration than the second chronic stimulation component.

In certain embodiments of an above-described method, the eating disorder is bulimia and the application of the first therapeutic stimulation signal, enhanced in some instances by the second therapeutic stimulation signal, alleviates binge eating and/or purging behavior in the individual. In some embodiments, the application of the signal(s) induces a feeling of satiety in the individual. In some embodiments, the selected area of the brain comprises at least a portion of the insula, or a white matter tract leading to a portion of the insula. In some embodiments, the selected area is chosen from the group consisting of the left and right anterior and posterior insula and the claustrum. In some embodiments, the selected area comprises a subcallosal area, or a white matter tract leading to a subcallosal area. In some embodiments, the selected area of the brain comprises at least a portion of a Brodmann area within the cingulate chosen from the group consisting of Brodmann area 24 and Brodmann area 25, or the selected area comprises a white matter tract leading to said Brodmann area. In some embodiments, the selected area of the brain includes at least a portion of a Brodmann area within the prefrontal cortex, or a white matter tract leading to that Brodmann area. For instance, the selected area may comprise the orbitofrontal cortex and/or at least a portion of any of Brodmann areas 8-11. In still other embodiments, the selected area of the brain comprises the thalamus, brainstem, cerebellum, or midbrain, or at least one nucleus therein, or a white matter tract leading to the nucleus. In some embodiments, the selected area comprises a pontine or medullary nucleus, such as the locus coeruleus, NTS, dorsal raphe or PBN. In some embodiments the selected area includes a parafascicular nucleus.

Chemical stimulation of the selected area of the brain is employed in accordance with certain embodiments an above-described method of the present invention. In some embodiments, the first stimulator comprises a chemical dispensing assembly including a catheter in communication with a pump, and the first therapeutic stimulation signal comprises a predetermined pumping signal. This method comprises coupling the catheter to the selected area of the individual's brain; and applying the first predetermined pumping signal to the chemical dispensing assembly such that the chemical is dispensed by the catheter and contacts the neural tissue, whereby the neuronal activity of the neural tissue is modified and such modification of neuronal activity alleviates a symptom of the eating disorder.

Cranial nerve stimulation together with deep brain sensing is employed in accordance with still other embodiments of the present invention for treating an individual suffering from an eating disorder. For instance a representative method of treatment includes (a) providing a controller comprising a signal generator and processor in communication with a first electrode and a second electrode; (b) coupling the first electrode to a cranial nerve of the individual; (c) coupling the second electrode to an area of the individual's brain selected from the group consisting of insula, subcallosal area, cingulate, thalamus, prefrontal cerebral cortex, brain stem, cerebellum, and white matter tracts leading from an aforementioned area; (d) applying a predetermined electrical signal to the first electrode; (e) sensing electrical activity in a selected area of the brain by the second electrode; (f) comparing the resulting sensed electrical activity to a predetermined electrical state of the selected area; and (g) determining from this comparison whether the application of the predetermined electrical signal to the first electrode causes a modulation of electrical activity of the brain area, wherein such modulation of electrical activity corresponds to alleviation of a symptom of an eating disorder. In certain embodiments, the cranial nerve is selected from the group consisting of vagus, hypoglossal, trigeminal and accessory nerves.

Also provided in accordance with certain embodiments of the present invention is a method of treating an individual suffering from an eating disorder by deep brain stimulation and cranial nerve sensing. This method comprises (a) providing a controller comprising a signal generator and processor in communication with a first electrode and a second electrode; (b) coupling the first electrode to a cranial nerve of the individual; (c) coupling the second electrode to an area of the individual's brain selected from the group consisting of insula, subcallosal area, cingulate, thalamus, prefrontal cerebral cortex, brain stem, cerebellum, and white matter tracts leading to an aforementioned area; (d) applying a predetermined electrical signal to the second electrode to modulate neuronal activity of the selected area of the brain; (e) sensing electrical activity in the cranial nerve by the first electrode; (f) comparing the resulting sensed electrical activity to a predetermined electrical state of the nerve; and (g) determining from such comparison whether the application of the predetermined electrical signal to the second electrode causes a modulation of electrical activity of the cranial nerve.

In accordance with certain embodiments of the invention, a method of treating an eating disorder such as bulimia is provided. The method comprises the steps of: surgically implanting an electrical stimulation lead having a proximal end and a stimulation portion, wherein after implantation the stimulation portion is in communication with a selected subcallosal area or a white matter tract leading to a subcallosal area; coupling the proximal end of the lead to a signal generator; and generating an electrical signal with the signal generator wherein the signal electrically stimulates the selected area thereby treating bulimia or other eating disorder. In some embodiments, the method further comprises surgically implanting a catheter having a proximal end coupled to a pump and a discharge portion for infusing a dosage of a pharmaceutical, wherein after implantation the discharge portion of the catheter is in communication with the selected subcallosal area or a white matter tract leading to a subcallosal area; and operating the pump to discharge the pharmaceutical through the discharge portion of the catheter into the selected subcallosal area, or white matter tract, thereby treating the eating disorder.

In accordance with another embodiment of the present invention, a method of treating an eating disorder comprises surgically implanting an electrical stimulation lead having a proximal end and a stimulation portion, wherein after implantation the stimulation portion is in communication with Brodmann area 25; coupling the proximal end of the lead to a signal generator; and generating an electrical signal with the signal generator wherein said signal electrically stimulates Brodmann area 25 thereby treating the eating disorder In certain embodiments, electrical stimulation of Brodmann area 25 results in modulation of neuronal activity in Brodmann area 25. In certain embodiments, electrical stimulation of Brodmann area 25 results in modulation of neuronal activity in Brodmann area 9. In certain embodiments, electrical stimulation of Brodmann area 25 results in modulation of neuronal activity in Brodmann area 24.

In certain embodiments, an above-described method further comprises the steps of: surgically implanting a catheter having a proximal end coupled to a pump and a discharge portion for infusing a dosage of a pharmaceutical, wherein after implantation the discharge portion of the catheter is in communication with Brodmann 25; and operating the pump to discharge the pharmaceutical through the discharge portion of the catheter into Brodmann area 25 thereby treating the eating disorder. In certain embodiments, the pharmaceutical is selected from the group consisting of inhibitory neurotransmitter agonists and antagonists, excitatory neurotransmitter agonists and antagonists, agents that increase the level of an inhibitory neurotransmitter, agents that decrease the level of an excitatory neurotransmitter, and local anesthetic agents.

Also provided in accordance with certain embodiments of the present invention is a method of treating an eating disorder comprising the steps of: surgically implanting an electrical stimulation lead having a proximal end and a stimulation portion, wherein after implantation the stimulation portion is in communication with a selected subgenual cingulate area or a white matter tract leading to a subgenual cingulate area; coupling the proximal end of the lead to a signal generator; and generating an electrical signal with the signal generator wherein said signal electrically stimulates the selected subgenual cingulate area, thereby treating the disorder.

Further provided in accordance with certain embodiments of the present invention is a method of treating an eating disorder comprising the steps of: surgically implanting an electrical stimulation lead having a proximal end and a stimulation portion, wherein after implantation the stimulation portion is in communication with either one of the cranial nerves or a subcallosal area, or a white matter tract leading to a subcallosal area; surgically implanting a catheter having a proximal end coupled to a pump and a discharge portion for infusing a dosage of a pharmaceutical, wherein after implantation the discharge portion of the catheter is in communication with the selected subcallosal area or white matter tract; and coupling the proximal end of the lead to a signal generator; generating an electrical signal with the signal generator wherein said signal electrically stimulates the selected subcallosal area; and operating the pump to discharge the pharmaceutical through the discharge portion of the catheter into the selected subcallosal area or white matter tract, thereby treating the eating disorder.

In accordance with a further embodiment of the present invention is provided a method of treating an eating disorder comprising the steps of: surgically implanting an electrical stimulation lead having a proximal end and a stimulation portion, wherein after implantation the stimulation portion is in communication with Brodmann area 25, or a white matter tract leading to that area; surgically implanting a catheter having a proximal end coupled to a pump and a discharge portion for infusing a dosage of a pharmaceutical, wherein after implantation the discharge portion of the catheter is in communication with the selected Brodmann area 25, or white matter tract leading to that area; and coupling the proximal end of the lead to a signal generator; generating an electrical signal with the signal generator wherein said signal electrically stimulates Brodmann area 25; and operating the pump to discharge the pharmaceutical through the discharge portion of the catheter into Brodmann area 25, or the selected white matter tract leading to that area, thereby treating the disorder.

In certain embodiments of any of the above-described methods, a sensor is provided and sensing occurs epidurally, subdurally, or on the scalp.

In certain embodiments of an above-described process, the electrical parameters are adjusted to bilaterally stimulate both vagus nerves, in synchrony or asynchronously, in order to selectively modulate (e.g., inhibit, excite, or block) selective areas of the brain to provide a therapeutic effect. For example, the device is adjusted to provide timing of bursts of electrical bilateral stimulation to attenuate the neural activity in selective areas of the brain. The parameters may be adjusted to beneficially modulate selective parasympathetic afferents of the cranial nerves to modulate the gustatory pathways, olfactory, pro-inflammatory or anti-inflammatory pathways, respiratory pathways, cardiac pathways, baroreceptor pathways, the somatosensory pathways, and satiety pathways. Similarly, cranial nerve stimulation may affect neurotransmitter pathways such as noradrenergic, serotoninergic, dopaminergic and cholinergic pathways.

In certain embodiments of an above-described method, an implanted stimulating and/or sensing electrode and/or a plurality of electrodes contacts or is in proximity to, one of the cranial nerves and/or a volume of neural tissue in the brain of an individual. The cranial nerve is preferably the trigeminal, hypoglossal, vagus and/or accessory nerve. The nerve may be contacted at any point along its length or one of the nerve branches. One or more of the cranial nerves may be stimulated/modulated and this may occur bilaterally, i.e. both left and right vagus nerves.

In an above-describe method, a system is employed which comprises an internal or external device or system for measuring, sensing, recording, monitoring the physiological activity, physiological event, physiological threshold, body or brain state. This is preferably accomplished by sensing electrical activity (action potentials) in a nerve or neural tissue in or from the brain.

Certain embodiments of an above-described method employ a device, equipment or system, that can vary the treatment parameters, based on adaptive learning whereby the device senses neuronal activity after stimulation and automatically adjusts the controller to attempt to deliver optimized therapy. The controller can also sense the result of adverse stimulation and adjust the stimulation to prevent an adverse patient response.

In accordance with still another embodiment of the present invention, a system for modulating neural tissue in a living person is provided which comprises a first electrode for electrically coupling to the neural tissue; a second electrode for electrically coupling to a cranial nerve of the patient; a source of electricity; a signal generator coupled to the electricity source and to the first and second electrode; and a programmable electronics package in communication with the signal generator, the system adapted to apply a first therapeutic electrical signal to the neural tissue by the first electrode, and to apply a second therapeutic electrical signal to the cranial tissue by the second electrode, wherein the first and second electrical signals cause modulation of neuronal activity of the neural tissue. In some embodiments the first signal comprises a first acute electrical signal component and a first chronic electrical signal component. In some embodiments the second signal comprises a second acute electrical signal component and a second chronic electrical signal component.

In certain embodiments of the present invention a system for modulating neural tissue in a living person is provided in which the system comprises a first electrode for electrically coupling to the neural tissue; second electrode for electrically coupling to a cranial nerve of the patient; a source of electricity; a signal generator coupled to the electricity source and to the first and second electrode; and a programmable electronics package in communication with the signal generator, the system adapted to apply a first therapeutic electrical signal to the neural tissue by the first electrode, and to apply a second therapeutic electrical signal to the cranial tissue by the second electrode, wherein the first and second electrical signals are selected to cause modulation of neuronal activity of the neural tissue.

In certain embodiments of the present invention a system for modulating neuronal activity in a volume of neural tissue in the brain of a living person is provided which comprises (a) a first electrode for electrically coupling to a selected area of brain neural tissue; (b) a second electrode for electrically coupling to a cranial nerve of the patient; a source of electricity; (c) a controller comprising a signal generator coupled to the electricity source and to the first and second electrode; and (d) a programmable electronics package in communication with the controller, the controller adapted to apply a therapeutic electrical signal to the cranial nerve by the second electrode, and to sense electrical activity of the brain neural tissue by the first electrode, the programmable electronics package comprising a comparator for comparing the sensed electrical activity in the brain tissue to a predetermined electrical state of the brain tissue. In certain embodiments the second electrical signal is selected to cause modulation of neuronal activity of the brain neural tissue. These and other embodiments, features and advantages will be apparent from the following description and drawings.

BRIEF DESCRIPTION OF THE DRAWINGS

FIGS. 4A-B are simplified illustrations of stimulator placement sites in selected areas of the brain of a patient for treatment of an eating disorder, in accordance with certain embodiments of the present invention.

DETAILED DESCRIPTION OF THE PREFERRED EMBODIMENTS

Definitions.

"Eating disorder" refers to any of a group of syndromes, including but not limited to anorexia nervosa, bulimia nervosa, and binge eating disorder. They are characterized by extreme disruptions in eating and intense anxiety over body weight or size.

As used herein, the terms "stimulating" and "stimulator" generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however for simplicity, the terms "stimulating" and "modulating," and variants thereof, are sometimes used interchangeably herein. The effect of delivery of the signal to the neural tissue may be excitatory or inhibitory and may potentiate acute and/or long-term changes in neuronal activity. For example, the effect of "stimulating" or "modulating" a neural tissue may comprise one or more of the following effects: (a) changes in neural tissue to initiate an action potential (bi-directional or uni-directional), (b) inhibition of conduction of action potentials (endogenous or externally stimulated) or blocking the conduction of action potentials (hyperpolarizing or collision blocking), (c) affecting changes in neurotransmitter/neuromodulator release or uptake, receptors, gated ion channels or synapses which can be excitatory, inhibitory or of a blocking nature, and (d) changes in neuro-plasticity or neurogenesis of brain tissue.

"Deep brain stimulation" (DBS) refers to direct or indirect application of a stimulus to an area within the brain. Such stimulation may be electrical, chemical (e.g., drug or pharmaceutical), or magnetic and may be applied directly or indirectly to the neural tissue of the brain. Similarly, deep brain sensing refers to the detection of an electrical or chemical signal from within the brain.

For ease of reference, "cranial nerve stimulation" is sometimes referred to herein simply as "VNS").

The terms "couple," "couples," "coupled," and "coupling" refer to either indirect or direct electrical connection.

"Predetermined electrical signal" refers to an electrical pulse, or pattern of electrical pulses, having defined parameters such as pulse current, pulse width, frequency, on-time and off-time.

"Satiety" refers to a feeling of sufficiency of dietary intake, a not-unpleasant lack of desire to continue eating or drinking, a full-stomach sensation.

"Chemical stimulation" and "chemical agent" refer to either chemical, drug or pharmaceutical agents capable of stimulating neuronal activity in a nerve or in neural tissue exposed to such agent. Examples of such agents are inhibitory neurotransmitter agonists, excitatory neurotransmitter antagonists, agents that increases the level of an inhibitory neurotransmitter, agents that decrease the level of an excitatory neurotransmitter, and local anesthetic agents.

Description.

The inventors propose that neural circuitry of the brain involved with satiety and with symptoms of bulimia and other eating disorders comprise neurons in certain areas of the brain that have not been previously correlated with causation or alleviation of eating disorders. These areas include the insula, subcallosal area, cingulate, thalamus, prefrontal cerebral cortex, brain stem, cerebellum, and white matter tracts leading to an aforementioned area or to a Brodmann area or nucleus therein. Those areas are believed to comprise nodes in the neural circuitry that relate to the manifestation of eating disorders, and may be modulated to affect the presence, absence or degree of an eating disorder in the individual. It is also proposed that sensing of neuronal activity may be employed in conjunction with modulation of one or more of those areas of the brain to adapt or modify stimulation parameters of a neurostimulation system and to optimize a therapeutic treatment regimen for treating an individual patient's eating disorder.

Deep Brain Stimulation (DBS) System for Treatment of Eating Disorders.

Figure 1:
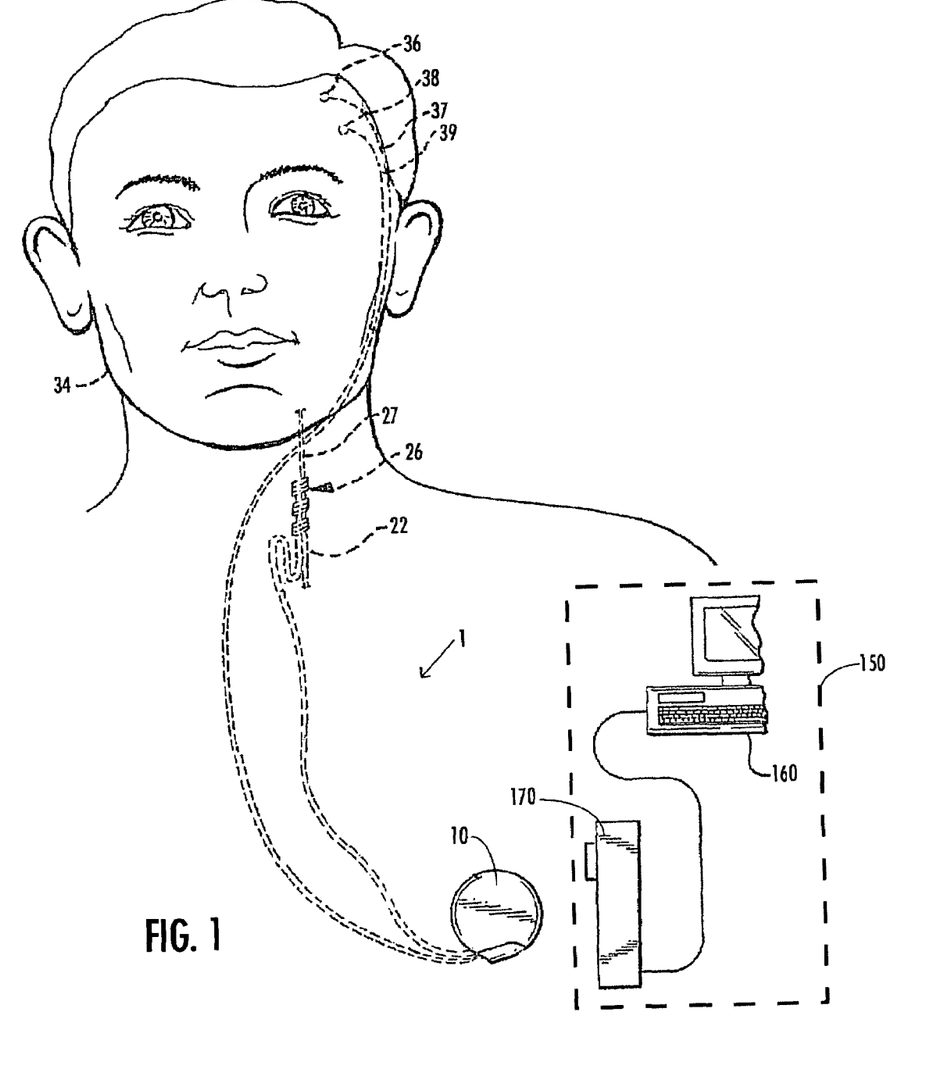
FIG. 1 is a simplified illustration of an electrode and neurostimulator placement configuration for treating an eating disorder in accordance with an embodiment of the present invention.

Referring to FIG. 1, a neurostimulator system 1 is shown as configured for treating bulimia or another eating disorder in a patient 34 (shown in phantom line) by modulating the electrical activity of selected areas of the brain that are associated with symptoms of the disorder. System 1 generally includes at least one implantable stimulator device (stimulator) 36, preferably an electrode, in communication with a microprocessor-based control device (controller) 10 for producing the stimulatory signals.

Figure 2:
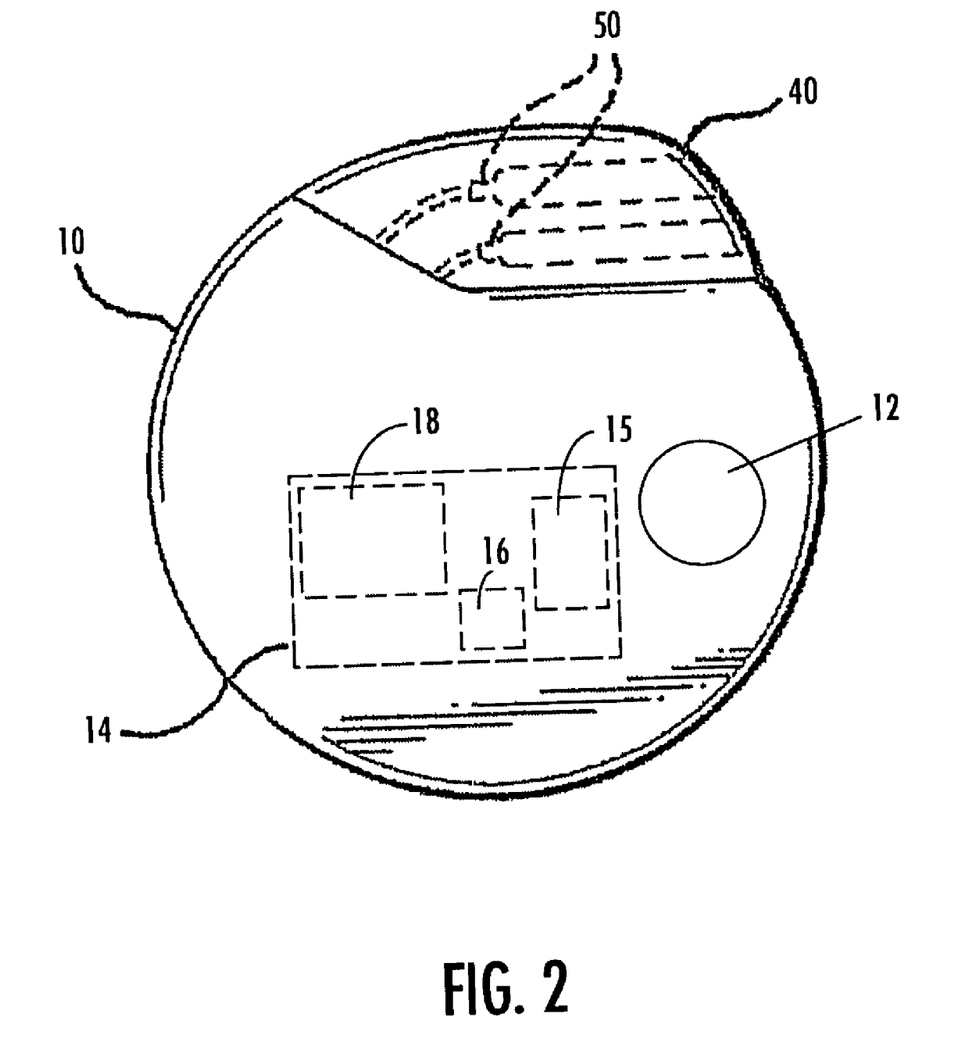
FIG. 2 is a fragmentary illustration of a controller containing a battery and programmable electronics package (shown as a block diagram), for use in treating an eating disorder in accordance with an embodiment of the present invention.

Stimulator. For ease of reference, the stimulator or stimulus applicator is sometimes referred to herein as simply "the electrode." It should be understood, however, that stimulation of a nerve or neural tissue can be electrically, magnetically or chemically/pharmaceutically mediated, or a combination of any or all of those modes. An electrode is designed for placing in direct contact with a volume of neural brain tissue to be stimulated and/or sensed, as may be required. Alternatively, at least one electrode is selected which is suitable for placement in proximity to the target neural tissue. For electrical stimulation mode, the controller 10 is coupled to each electrode 36 by transcranial lead(s) 37, and is designed for applying an electrical signal to the selected area using the electrical signal generator unit 15 of controller 10 (FIG. 2). Lead(s) 37, 39 attach to the controller at connectors 50 of header 40. Electrode/lead assemblies of this type are commercially available from known suppliers. Alternatively, lead(s) 37 is/are omitted and at least one implanted electrode comprises an induction receiver and controller 10 is configured to remotely modulate the target neural tissue through telemetry via an external transmitter. A suitable electrode of this type is commercially available from known suppliers.

Sensor. The system may include at least one implantable sensing electrode (sensor) 38. The sensor is designed to measure endogenous neural activity or activity induced by modulation through actions of the controller 10 and is in communication with the control device 10 via lead(s) 39. Accordingly, the system may be adapted for applying the stimulation signal in response to a preselected triggering event, from sensed physiological activity, from an external actuator, from brain imaging data or from physician or patient input, as discussed in more detail below. Suitable sensing electrodes and other sensing devices capable of sensing physiological parameters are commercially available from known sources.

Controller. Certain parameters of the stimuli generated by the controller are programmable. System 1 comprises an internal or external system capable of measuring, sensing, recording, monitoring the physiological activity, physiological event, physiological threshold, body or brain state. Additionally, the system may be designed to vary the treatment parameters, based on adaptive learning whereby the device senses activity or physiologic changes after stimulation and automatically adjusts the controller to attempt to deliver optimized therapy. In that case, the controller can also sense the result of adverse stimulation and adjust the stimulation to prevent an adverse patient response.

As shown in FIG. 1, an external programming system 150 is employed in a conventional manner for implantable electrical medical devices. External programming system 150 is preferably capable of wireless (e.g., radio frequency) communication with the controller 10, and comprises a computer 160 and a wand 170 having an RF transmitter and receiver. Computer 160 may comprise a handheld computer operable by a healthcare provider. Wand 170 is capable of communicating with a receiver and transmitter in controller 10, and may be used to receive data from or transmit data to the controller 10.

Figure 5:
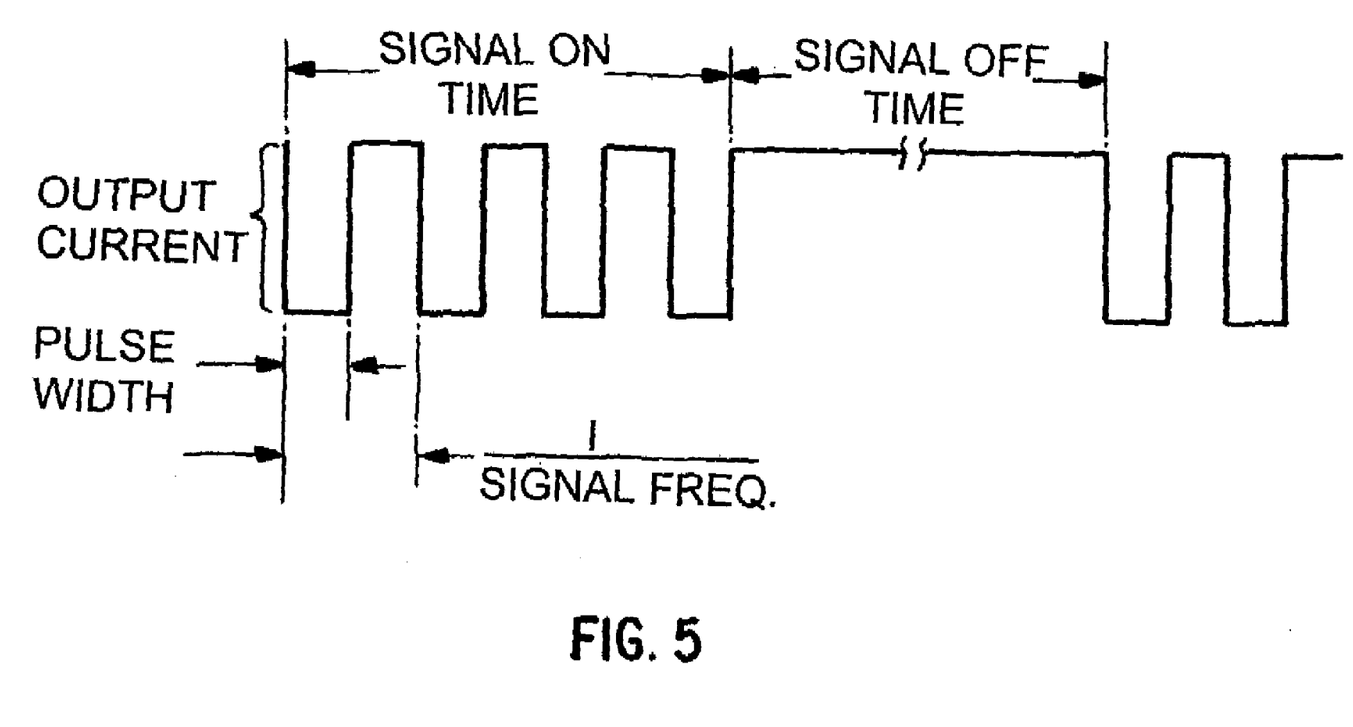
FIG. 5 is an illustration of an electrical output signal waveform of the signal generator of FIG. 1 useful for clarifying relevant parameters of the signal developed by the signal generator for application to the nerve, according to an embodiment of the present invention.

Alternatively, the implantable control device 10 comprises a programmable electronics package 14 containing a signal generator15, a monitoring unit (monitor) 16 for transmitting control signals to/from the implanted electrode(s) and sensor (s), as appropriate, and a processing unit (processor) 18 for recording, measuring, sensing or monitoring physiologic data and comparing it to stored values, baseline values, reference or expected values and performing calculations on best treatment parameters (as schematically illustrated in FIG. 5). A power source 12 is also contained in controller 10. The programmable processor is configured to adjust and transmit stimulus parameters to the stimulator assembly in order to treat the disorder. The monitoring data can be stored digitally for future processing or diagnosis. A generally suitable form of implantable controller/pulse generator for use in the system and method of the present invention is disclosed, for example, in U.S. Pat. No. 5,154,172, assigned to the same assignee as the instant application (the device also referred to as a NeuroCybernetic Prosthesis or NCP device (NCP is a trademark of Cyberonics, Inc. of Houston, Tex., U.S.A.)

Figure 3:
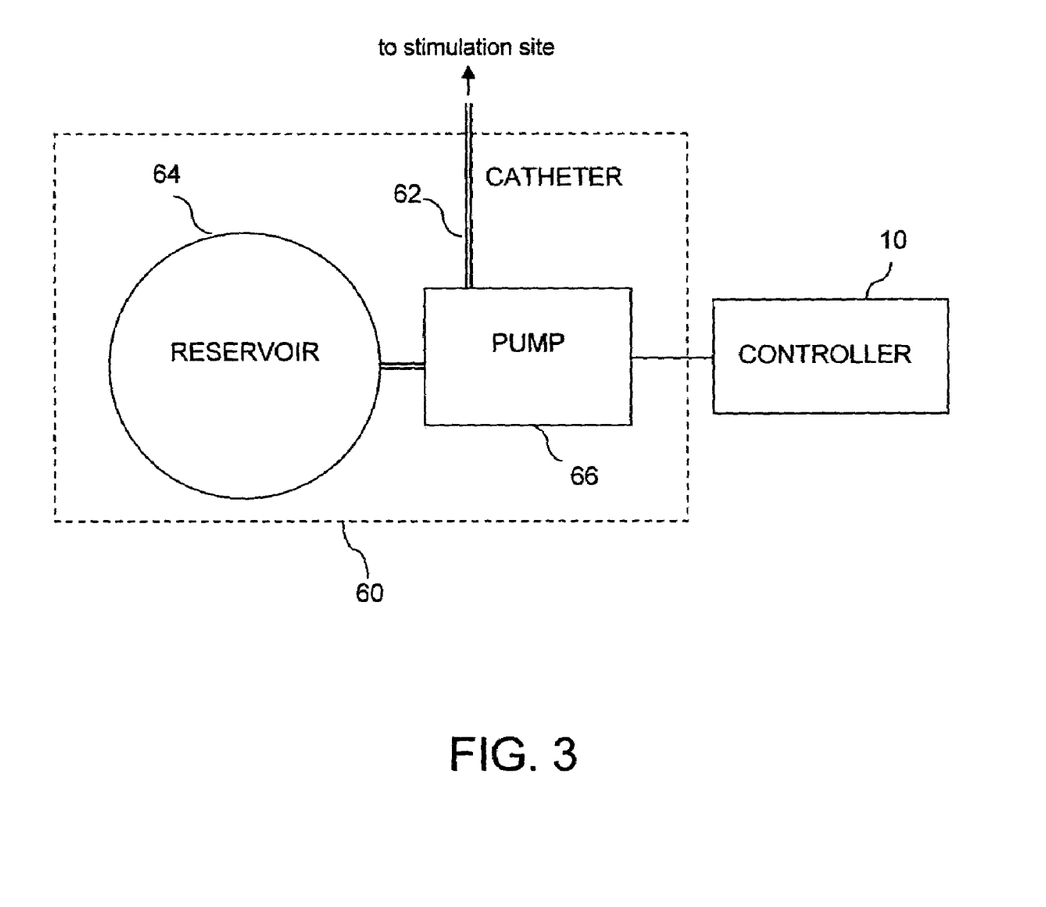
FIG. 3 is a schematic block diagram showing a chemical stimulation assembly according to an embodiment of the present invention.

Electrical, chemical, magnetic stimulation. Although the use of at least one electrode as the stimulus application device (stimulator) for delivering electrical stimulation to the target neural tissue is preferred, it is also contemplated that the neurostimulator system could instead, or additionally, include a chemical or pharmaceutical applicator for applying a therapeutic stimulus to the target neural tissue effective to modulate the activity of the neural tissue to ameliorate the eating disorder. The chemical stimulus application device 60 may comprise a catheter 62, chemical-filled reservoir 64 and a pump 66 that is either implantable or has both implantable (catheter) and external (pump) components, or another suitable chemical delivery device could be included in the system (FIG. 3). The pump is in communication with controller 10. Examples of the types of chemicals or drugs that may be beneficially employed are inhibitory neurotransmitter agonists or antagonists, excitatory neurotransmitter agonists or antagonists, chemicals that increases the level of an inhibitory neurotransmitter, chemicals that decrease the level of an excitatory neurotransmitter, and local anesthetics. Control signals may be transmitted to or from either an electrode on the nerve, electrode or sensor in the brain, from a chemical delivery device and/or sensor, or from an internal or external monitoring unit via telemetry and/or through signals transmitted through conductive leads, as provided in the programmable circuitry.

In another configuration of the neurostimulation system, the stimulator is omitted and the system is designed for non-invasively applying a magnetic stimulus to a selected nerve or neural tissue from an external source via a transcranial magnetic stimulator (not shown), as are known in this field. Accordingly, it should be appreciated that neural tissue modulation can be electrically, magnetically or chemically/pharmaceutically mediated.

Still another configuration of the neurostimulation system substitutes an electrode designed for dural or subdural placement adjacent an area of the brain such as the orbitofrontal cortex area, instead of using an electrode for deep brain implantation. Dural or subdural electrodes may be designed for applying electrical stimulation or for sensing electrical activity, or both.

In still another configuration of the system, also shown in FIG. 1, the neurostimulation system includes at least one stimulator and/or sensor for coupling directly or indirectly to at least one cranial nerve, preferably the trigeminal, hypoglossal, vagus and accessory nerve. Alternatively, electrodes suitable for placement on, or proximal to, the left and/or right vagus nerve(s) in a near-diaphragmatic location (e.g., supradiaphragmatic or subdiaphragmatic) may be included in the system. These may be stimulating and/or sensing electrodes.

Programmable control. The control device is designed so that control signals are transmitted from an internal or external monitoring unit to the electrode(s) and/or sensor(s). The system is capable of delivering stimulation that can be intermittent, periodic, random, paired-pulses, coded or patterned. For example, electrical stimulation frequency can be 0.1 to 2500 Hz, pulse width 1-2000 micro seconds, current amplitude 0.1 mA to 10 mA. Stimulation can occur through either the cathode (−) electrode or positive (+) electrode.

The neurostimulation system 1 is preferably capable of delivering to the target neural tissue a stimulatory electrical signal that can be intermittent, periodic, random, paired-pulses, coded or patterned. Stimulation frequency can be 0.1 to 2500 Hz, pulse width 1-2000 micro seconds, current amplitude 0.1 mA to 10 mA. Stimulation can occur through either the cathode (−) electrode or positive (+) electrode.

Manual activation/deactivation. The system design may be varied to provide a manual activation or deactivation switch in association with controller 10. Similar devices for manual and automatic activation of implantable medical devices are known, such as are disclosed in U.S. Pat. No. 5,304,206 (Cyberonics, Inc.). For example, manual activation or deactivation of the signal generator is achieved using a device such as an accelerometer or a piezoelectric element mounted to the inner surface of the controller housing so as to detect light taps by the patient on the controller implant site in the patient's body. This design provides for the patient to have limited but convenient control over the device operation, to the extent that the physician determines is appropriate.

Method of Treating an Eating Disorder

FIG. 1 illustrates a preferred location of implanted controller 10 in the patient's chest in a cavity formed by the implanting surgeon just below the skin, much as a pacemaker pulse generator would be implanted. A representative treatment regimen to assist a patient in overcoming a serious eating disorder (e.g., repeated episodes of binge eating and purging) generally includes obtaining an above-described neurostimulation system that is configured and programmed or programmable to modulate neuronal activity of a predetermined area of neural tissue.

Figure 4A:
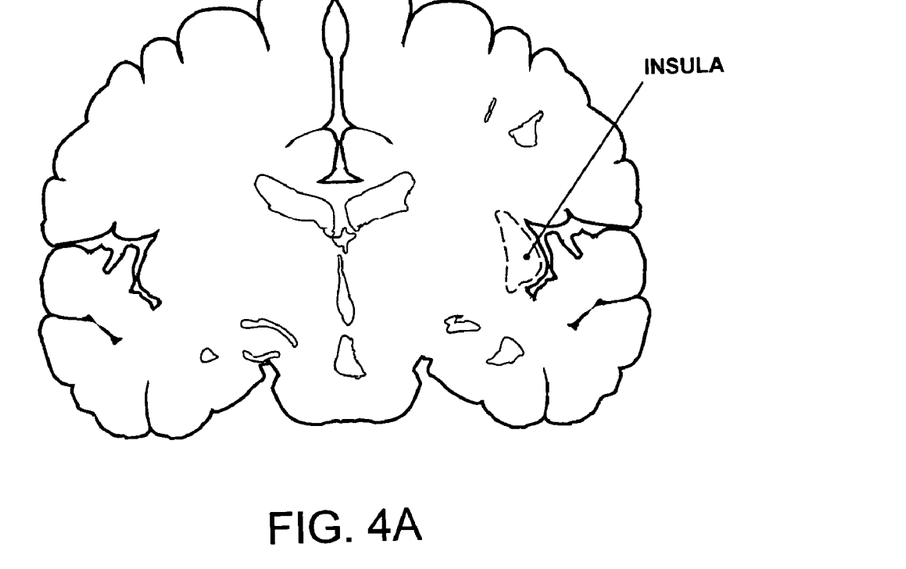
FIG. 4A is a sagittal sectional view of the brain depicting a representative insula stimulation site of the brain.
Figure 4B:
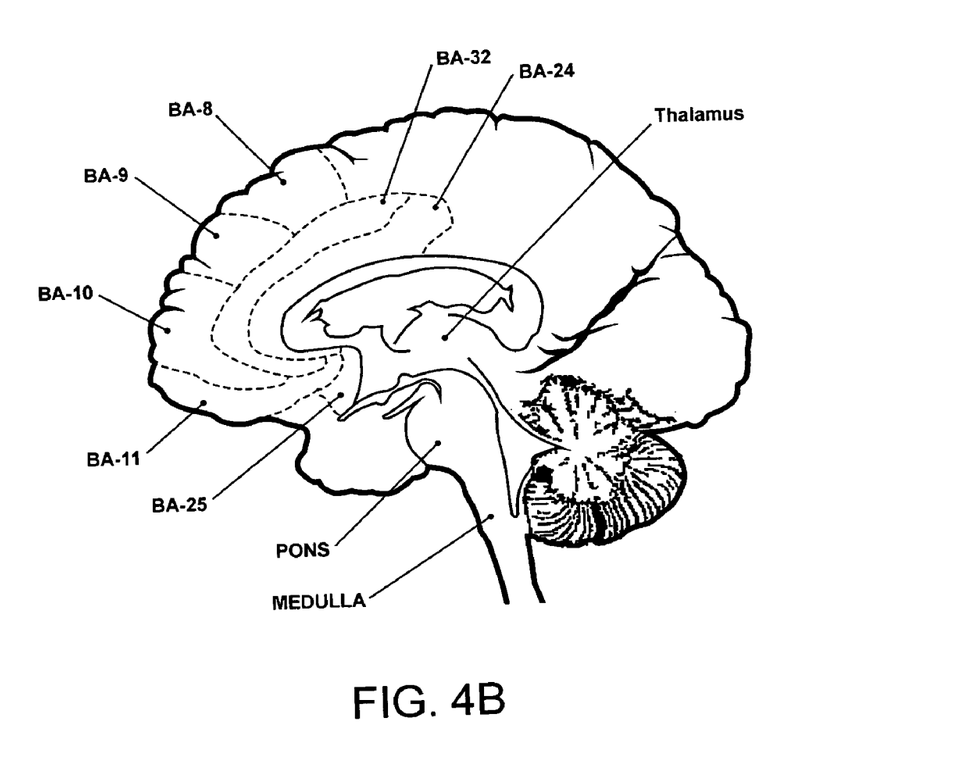
FIG. 4B is a coronal sectional view of the brain depicting representative prefrontal cortex, cingulate, thalamus and brain stem treatment sites.

At least one stimulator 36 (e.g., electrode, catheter) is surgically implanted in the brain of a patient in need of treatment for a serious eating disorder. Employing appropriate surgical techniques as are known in the art, a small opening is made in the skull and the stimulator is placed in, or proximal to, an area of the brain that comprises a "node" in the neural circuitry which is correlated with symptoms of the patient's eating disorder. For example, the target area may be associated with a feeling of satiety in the patient. A representative stimulator implantation location is a site in the insula, as indicated in FIG. 4A. The left and right anterior and posterior insula and the claustrum are preferred modulation sites. Other preferred stimulator implantation sites are the subcallosal area, cingulate, thalamus, prefrontal cortex, cerebellum, midbrain and brainstem, and the nuclei or Brodmann areas within those regions, and white matter tracts leading to or from any of those areas (FIG. 4B). Brodmann areas 24, 25 and 32, or a portion of any of those, are preferred stimulation sites. The parafascicular nucleus is another preferred site. Brodmann areas 8, 9, 10 and 11, and the orbitofrontal cortex, or a portion of one or more of those areas are also preferred sites. The pontine and medullary regions are also suitable implantation sites. While the figures and description focus on one hemisphere of the brain, it should be understood that stimulation and/or sensing of like structures on either or both sides of the brain is also contemplated. Stimulation and/or sensing may be applied to sites in one or both hemispheres and may be carried out in at the same time or at different times, and may comprise the same or different stimuli. Areas of the brain that are of interest as stimulation and/or sensing sites include, but are not limited to, centromedian fascicular complex, hippocampus, ventral medial Vim thalamic nucleus, parafascicular complex, other portion of the thalamus, entirety of the thalamus, subthalamic nucleus (STN), caudate, putamen, other basal ganglia components, cingulate gyros, other subcortical nuclei, nucleus locus ceruleus, pedunculopontine nuclei of the reticular formation, red nucleus, substantia nigra, other brainstem structure, cerebellum, internal capsule, external capsule, corticospinal tract, pyramidal tract, ansa lenticularis, limbic circuit of Papez, the fronto-basal ganglionic-thalamo-cortical system, white matter tracts, motor cortex, premotor cortex, somatosensory cortex, other sensory cortical regions, Broca's area, Wernickie's area, ventricular region, paraventricular region, other central nervous system structure, other peripheral nervous system structure. The cortex, limbic system and reticular system, pre-frontal cortex, orbitofrontal cortex, anterior limb of the internal capsule, nucleus accumbens, ventral striatum, the ventral pallidum anterior nucleus of the thalamus, dorsomedial nucleus of the thalamus, intralaminar thalamic nuclei, the cingulate cortex, amygdala, hippocampus, mamillary bodies, the lateral hypothalamus, the locus ceruleus, the dorsal raphe nucleus, parabrachial nucleus (PBN), nucleus of the solitary tract (NTS), the caudal ventrolateral medulla (CVL), and rostral ventrolateral medulla (RVL), paraventricular nucleus of the hypothalamus, parafascicular nucleus, the bed nucleus of the stria terminalis, the prefrontal cortex, the supraoptic nucleus, and forebrain circumventricular organs, ventral tegmentum, the substantia nigra, pars compacta and reticulate.

In electrical stimulation mode, the implanted electrode is coupled to the signal generator of controller 10. As schematically shown in FIG. 3, for chemical/drug stimulation mode, a catheter couples the target tissue to a chemical/pharmaceutical delivery assembly (pump) that communicates with the controller 10. Leads 37,39 are preferably routed under the scalp to an implanted controller 10, however they could also be routed externally to an implanted or external controller. A catheter may also be similarly routed to an implanted or externally located pump. A catheter that also includes at least one electrode may also be employed, if desired.

The system may include a sensing capability that may be operated to detect electrical or chemical activity in a selected area of the brain or volume of neural tissue, providing feedback to the controller so that the stimulation signal (e.g., one or more parameters such as pulse current, pulse width, frequency, and on-time or off-time) is automatically adjusted, thereby enhancing treatment of the eating disorder. Preferred areas of the brain for sensing are the insula, subcallosal area, cingulate, thalamus, hypothalamus, prefrontal cortex, cerebellum, midbrain and brainstem, the nuclei within those regions, and white matter tracts leading from any said area. A stimulation electrode may also serve as a sensing electrode. Preferably the sensing of a brain area is obtained epidurally, subdurally, or on the patient's scalp. Alternatively, at least one sensing electrode 26, or other sensing device, is placed in contact with, or in proximity to, one of the cranial nerves 27. The sensor is coupled to the controller 10 via lead 22 (FIG. 1). The selected cranial nerve being preferably the trigeminal, hypoglossal, vagus and/or accessory nerve. The nerve may be contacted at any point along its length or one of the nerve branches.

After sufficient healing from the surgical implantation procedure has taken place the physician selects appropriate stimulation signals by actuating neurostimulation system 1 to generate electrical stimuli in the form of electrical impulses according to a programmed regimen for deep brain stimulation of the selected area of the patient's brain. During the electrode implantation procedure, the physician checks the current level of the pulsed signal to ascertain that the current is adjusted to a magnitude at least slightly below a threshold of the patient at which adverse effects would occur. Typically, the stimulation level is programmed such that the patient does not experience significant adverse effects attributable to the DBS therapy, although variations in device parameters settings may be observed from patient to patient. In any event, the maximum amplitude of the current should be adjusted accordingly until a beneficial effect (e.g., alleviation of urge to overeat), with a suitable safety margin. The adverse effects and/or beneficial effects thresholds may change noticeably with time over a course of days after implantation, so the levels are preferably checked again in the first few days after implantation to determine whether any adjustment is necessary to maintain an effective regimen. The DBS regimen preferably employs an intermittent pattern of a period in which a repeating series of pulses is generated for stimulating the selected neural tissue in the brain, followed by a period in which no pulses are generated. The on/off duty cycle of these alternating periods of stimulation and no stimulation preferably has a ratio in which the off time is approximately 1.8 times the length of the on time. Preferably also, the width of each pulse is set to a value not greater than about 500 microseconds, and the pulse repetition frequency is programmed to be in a range of about 130 Hz. The above-described electrical and timing parameters of the stimulating signal used for DBS are merely exemplary and do not constitute a limitation of the scope of the present invention.

As an aid to adjusting the programming of the system and optimizing the stimulating signal parameters for a particular patient's therapeutic regimen, a program of cranial nerve stimulation with selective deep brain sensing may be employed. This method includes placing an electrode in contact with, or in proximity to, one of the cranial nerves (preferably the left vagus nerve in the neck of the patient), and contacting a sensing electrode with a selected area of the patient's brain such as the insula, subcallosal area, cingulate, thalamus, hypothalamus, prefrontal cerebral cortex, brain stem, cerebellum, and white matter tracts leading from an aforementioned area. Both electrodes are in communication with a controller/stimulus generator/processor unit, as described above. A predetermined electrical signal is applied to the cranial nerve electrode, causing stimulation or inhibition (modulation) of the electrical activity of the neural tissue that receives an electrical stimulus from that cranial nerve. An illustrative idealized electrical output signal waveform of the signal generator useful for clarifying relevant parameters of the signal developed by the signal generator for application to the nerve is shown in FIG. 5. The programming and settings of the controller/processor are adjusted to provide timing of bursts of electrical stimulation to the nerve, causing selective parasympathetic afferents of the cranial nerves to be stimulated, whereby one or more of the gustatory pathways, olfactory, pro-inflammatory or anti-inflammatory pathways, respiratory pathways, cardiac pathways, baroreceptor pathways, the somatosensory pathways, and satiety pathways are beneficially activated, causing a responsive attenuation of neural activity in various areas of the brain. Similarly, cranial nerve stimulation may affect neurotransmitter pathways such as noradrenergic, serotoninergic, dopaminergic and cholinergic pathways.

The responsive modulation or change in electrical activity of the neuronal tissue in the area of the patient's brain contacted by the implanted electrode is sensed and communicated to the controller 10. Alternatively, programming of the system and optimizing of the stimulating signal parameters for the patient's therapeutic regimen includes executing a program of selective DBS with selective deep brain sensing. For instance, a sensor is implanted in communication with a subcallosal area, and the system is then operated to sense electrical or chemical activity in the subcallosal area providing feedback to the controller to optimally adjust the stimulation for treating the patient's eating disorder. The stimulatory and sensed data is analyzed in the processor to determine any change in electrical activity of the selected brain area caused by application of a particular electrical signal. In this way, the signal parameters are adjusted under the supervision of the physician causing a responsive attenuation of neural activity in selective areas of the brain. Such modulation of electrical activity of the selected area of the brain is correlated by the processor with observed or expected alleviation of a symptom of the patient's eating disorder.

The patient's eating behavior should be allowed to stabilize at approximately the preoperative level before the DBS regimen is actually administered. Treatment applied in the form of chronic intermittent electrical stimulation over each twenty-four hour period may be observed initially to result in no change in inappropriate eating/purging behavior of the patient. But after a period of several days of this DBS regimen, a discernible loss of interest in binge eating/over eating/purging will occur. A typical result may be that mealtime consumption tends to stretch over a considerably longer period of time than that observed for the patient's preoperative behavior, with smaller quantities of food intake in the course of a single meal separated by longer intervals of no consumption between meals. The DBS treatment is not expected to adversely affect normal behavior in other aspects of the patient's life. A complete suspension of the DBS regimen would be expected to result in a relatively rapid return to the previous bulimic behavior, ending after resumption of the DBS regimen. It is proposed that DBS stimulation of certain areas of the brain of individuals suffering from serious eating disorders may be a viable option for more effectively treating and changing inappropriate eating patterns and behavior in persons suffering from bulimia and other eating disorders.

Selective Stimulation of a Subcallosal Area. In a representative treatment regimen, a predetermined stimulatory signal (e.g., electrical signal) is applied to a subcallosal area of the person's brain, and such stimulation of a subcallosal area produces modulation of neuronal activity in a subgenual cingulate area. By application of another predetermined stimulatory signal, stimulation of the selected subcallosal area results in modulation of neuronal activity in the areas selected from the group consisting of Brodmann area 32, Brodmann area 25, Brodmann area 24, Brodmann area 10, and Brodmann area 9, as illustrated in FIG. 4B. As a result of such neuronal modulation of the selected subcallosal area, the frequency of the subject's desire to binge eat/purge is diminished. For instance, the stimulation portion (electrode) is in communication with Brodmann area 25, and an electrical signal stimulates Brodmann area 25 resulting in modulation of neuronal activity in Brodmann area 25, whereby the patient experiences a feeling of satiety and/or the urge to binge eat/purge is diminished. Another treatment regimen comprises applying a predetermined electrical signal to Brodmann area 25 which results in modulation of neuronal activity in Brodmann area 9. Still another predetermined electrical signal is applied to Brodmann area 32, Brodmann area 25 which results in modulation of neuronal activity in Brodmann area 24.

In chemical/pharmaceutical stimulation mode, the physician surgically implants a catheter having a proximal end coupled to a pump and a discharge portion for infusing a dosage of a chemical or drug, such that after implantation the discharge portion of the catheter is in communication with a subcallosal area. Application of the predetermined stimulation signal comprises operating the pump to discharge the chemical/drug through the discharge portion of the catheter into a subcallosal area, thereby treating the eating disorder. Targeted neural tissue and the affected (modulated) neural tissue may be the same or different, depending on the selected chemical/pharmaceutical stimulation signal, similar to the above-described electrical stimulation mode. For instance, the protocol may include surgically implanting a catheter having a proximal end coupled to a pump and a discharge portion for infusing a dosage of a pharmaceutical, wherein after implantation the discharge portion of the catheter is in communication with Brodmann 25 of the patient's brain. The predetermined stimulation signal is applied by operating the pump to discharge the pharmaceutical through the discharge portion of the catheter into Brodmann area 25 thereby modulating neural activity in that part of the brain to ameliorate symptoms of the eating disorder. Some applicable types of chemicals and/or pharmaceutical agents include inhibitory neurotransmitter agonists, excitatory neurotransmitter antagonists, agents that increases the level of an inhibitory neurotransmitter, agents that decrease the level of an excitatory neurotransmitter, and local anesthetic agents.

Selective Stimulation of an Insula Area. As indicated in FIG. 4A, another preferred treatment regimen comprises surgically implanting in the brain of a patient suffering from a serious eating disorder a stimulation lead having a proximal end and a stimulation portion, wherein after implantation the stimulation portion is in communication with a portion of the insula. The proximal end of the lead is coupled to a signal generator, which generates a predetermined electrical stimulation signal such that the signal electrically stimulates the selected insula area thereby modulating the neuronal activity of the affected tissue to ameliorate the eating disorder.

Selective Stimulation of a Subgenual Cingulate Area. As indicated in FIG. 4B, another preferred treatment regimen comprises surgically implanting an electrical stimulation lead having a proximal end and a stimulation portion, wherein after implantation the stimulation portion is in communication with a subgenual cingulate area. The proximal end of the lead is coupled to a signal generator that generates a predetermined electrical stimulation signal whereby the signal electrically stimulates the subgenual cingulate area to modulate the neuronal activity of the affected tissue which, in turn, ameliorates the eating disorder.

Selective Bimodal Stimulation—Electrical/Chemical DBS. Another treatment regimen includes both electrical and chemical stimulation modes. The physician surgically implants an electrical stimulation lead having a proximal end and a stimulation portion, wherein after implantation the stimulation portion is in communication with a subcallosal area of the person's brain. The physician also surgically implants a catheter having a proximal end coupled to a pump and a discharge portion for infusing a dosage of a chemical or a pharmaceutical agent, such that after implantation the discharge portion of the catheter is in communication with a selected subcallosal area. The proximal end of the lead is coupled to a signal generator, and a predetermined electrical signal is generated by the signal generator such that the selected subcallosal area is stimulated. Additionally, the pump is operated to discharge the chemical or pharmaceutical agent through the discharge portion of the catheter into a subcallosal area such that a subcallosal area is additionally stimulated by the chemical or pharmaceutical agent, to enhance alleviation of the eating disorder.

An exemplary procedure in which DBS and cranial nerve stimulation are employed together includes coupling a first electrode to a selected area of the patient's brain that is known or expected to be associated with eating disorder symptoms (e.g., a cingulate area or an insula area). A second electrode is coupled to a cranial nerve of the patient. A predetermined therapeutic electrical signal is applied to the first electrode, to stimulate the neural tissue, and a second predetermined therapeutic electrical signal is applied to the second electrode. As a result of the dual application of the first and second signals, advantageous modulation of the neuronal activity of the selected area of neural tissue is obtained which ameliorates bulimia or another eating disorder.

Another bimodal stimulation regimen comprises surgically implanting a stimulator electrode in direct or indirect communication with Brodmann 25. A catheter, having a proximal end coupled to a pump and a discharge portion for infusing a dosage of a pharmaceutical, is surgically implanted such that the discharge portion of the catheter is also in communication with Brodmann area 25. A predetermined electrical signal is applied to the electrode such that the Brodmann area 25 is stimulated. Additionally, the pump is operated to discharge the pharmaceutical agent through the discharge portion of the catheter into Brodmann area 25 such that Brodmann 25 is additionally stimulated, to enhance alleviation of the disorder. Electrical and chemical stimulation may be applied simultaneously or sequentially, as determined by the physician.

Selective DBS with Feedback Sensing. When a sensing capability is included, the implantable or external processor is additionally configured for measuring, sensing, recording, monitoring the physiological activity, physiological event, physiological threshold, body or brain state. This is accomplished, for instance, by sensing electrical activity in the nerve (action potentials), in or from the brain, heart, gastrointestinal tract, pancreas or other organs innervated by the vagus nerve. The processor and controller are configured such that the treatment parameters can be varied or adjusted based on adaptive learning, whereby the system detects activity or physiologic changes after stimulation and automatically adjusts the controller to attempt to deliver optimized therapy.

The controller/processor can also determine the result of adverse stimulation and adjust the stimulation to prevent an adverse patient response.

An exemplary adaptive brain stimulation system comprises at least one biological sensor coupled to a patient for sensing a present state of at least a first brain region or a first set of brain regions. At least one stimulating circuit is coupled with a first brain region or a first set of brain regions of the patient by a first electrode to carry out stimulation according to a set of stimulation parameters. The system also comprises a comparator coupled with the sensors to receive data related to the present state and compare the present set data with reference state data, wherein the comparison leads to a positive outcome or a negative outcome, wherein a positive outcome is a beneficial effect and/or the absence of unacceptable adverse effects. The at least one control circuit coupled with said at least one stimulating circuit is able to be adjusted according to the outcome of comparing the present and reference states, to control the set of stimulation parameters.

Cranial Nerve Stimulation with Selective Deep Brain Sensing. In a variation of the foregoing bimodal stimulation method, cranial nerve stimulation (VNS) is employed instead of, or in addition to, deep brain stimulation (DBS). In this variation of the method, one of the cranial nerves is electrically stimulated instead of electrically stimulating a subcallosal area. At least one stimulation electrode or chemical/drug stimulation assembly is placed in contact with, or in proximity to, one of the cranial nerves The selected cranial nerve is preferably the trigeminal, hypoglossal, vagus or accessory nerve. The nerve may be contacted at any point along its length or one of the nerve branches. For instance, as illustrated in FIG. 1, electrode 26 is preferably a bipolar stimulating electrode, preferably of the helical type described in U.S. Pat. No. 4,573,481 (Bullara). The electrode assembly is surgically implanted on the vagus nerve 27 in the patient's neck. As another example, the physician surgically may implant a pair of stimulation electrodes on the left and right vagus nerve and the stimulation signal parameters are adjusted to bilaterally stimulate both vagus nerves, in synchrony or asynchronously, in order to selectively inhibit, excite, or block selective areas of the brain to alleviate bulimia symptoms. The controller/processor is adjusted to provide timing of bursts of electrical bilateral stimulation to attenuate the neural activity in selective areas of the brain to achieve the desired result. The signal parameters may be adjusted so as to stimulate selective parasympathetic afferents of the cranial nerves, whereby one or more of the gustatory pathways, olfactory, pro-inflammatory or anti-inflammatory pathways, respiratory pathways, cardiac pathways, baroreceptor pathways, the somatosensory pathways, and satiety pathways are beneficially modulated. Similarly, cranial nerve stimulation may affect neurotransmitter pathways such as noradrenergic, serotoninergic, dopaminergic and cholinergic pathways.

A cranial nerve stimulation configuration is especially useful for optimizing the stimulating signal parameters, as mentioned above. For example, an electrode 26 is coupled to a cranial nerve (e.g., the vagus, hypoglossal, trigeminal or accessory nerve) of the individual, and communicates with controller 10 via lead 22. Another electrode 38, a sensing electrode or "sensor," is coupled to a selected area of the patient's brain such as a portion of, or a nucleus within, the insula, subcallosal area, cingulate, thalamus, hypothalamus, prefrontal cerebral cortex, brain stem, cerebellum, or a white matter tract leading to an aforementioned area. Depending on the location of the selected site in the brain, a less invasive subdural electrode may be employed rather than a depth electrode. Electrode 38 is also in communication with a controller/stimulus generator/processor unit. A predetermined electrical signal is applied to the cranial nerve electrode, causing stimulation or inhibition (modulation) of the electrical activity of the neural tissue that receives an electrical stimulus from that cranial nerve. The responsive modulation or change in electrical activity of the neuronal tissue is sensed by the implanted electrode and communicated to the controller/processor 10. The data is analyzed in the processor to determine whether application of a particular electrical signal causes a change in electrical activity of the selected brain area. Such modulation of electrical activity of the selected area is also correlated by the processor with subjective or objective data indicating alleviation of a symptom of an eating disorder.

Combined DBS and VNS. An exemplary procedure in which deep brain stimulation (DBS) and cranial nerve stimulation (VNS) are employed together includes coupling a first electrode to a cranial nerve of the patient. FIG. 1 illustrates an electrode coupled to a patient's left vagus nerve in the neck. Another placement configuration for one or more electrodes is a near-diaphragmatic location on the left and/or right vagus nerves, above or below the diaphragm, as is known and described in the literature. A second electrode is coupled to a selected area of the patient's brain that is known or expected to be associated with symptoms of an eating disorder (e.g., a subcallosal area). A predetermined therapeutic electrical signal is applied to the first electrode, to stimulate the cranial nerve, and a second predetermined therapeutic electrical signal is applied to the second electrode to stimulate the neural tissue. As a result of the dual application of the first and second signals, advantageous modulation of the neuronal activity of the selected area of neural tissue is obtained which ameliorates bulimia or another eating disorder. The stimulation parameters may be adjusted to bilaterally stimulate both vagus nerves, in synchrony or asynchronously, in order to selectively modulate (e.g., inhibit, excite, block) selective areas of the brain to provide the desired alleviation of symptoms of the eating disorder. The controller may be adjusted to provide timing of bursts of bilateral electrical stimulation to cause attenuation of neural activity in selective areas of the brain.

Combined DBS/VNS—Bimodal Electrical/Chemical Stimulation.

Another representative combined DBS/VNS treatment includes surgically implanting an electrode and lead assembly having a proximal end and a stimulation portion, wherein after implantation the stimulation portion (i.e., electrode) is in communication with either a cranial nerve or a subcallosal area. The physician also surgically implants a catheter having a proximal end coupled to a pump and a discharge portion for infusing a dosage of a chemical agent. After implantation the discharge portion of the catheter is in communication with the selected subcallosal area. The physician couples the proximal end of the lead to a signal generator. An appropriate electrical signal is created using the signal generator and is applied via the electrode and lead assembly, causing the signal to electrically stimulate a subcallosal area. In concert with the electrical stimulation, the pump operated to discharge the chemical agent through the discharge portion of the catheter into the selected subcallosal area, thereby treating the eating disorder.

Similarly, the physician may surgically implant an electrode/lead assembly such that, after implantation, the stimulation portion is in communication with Brodmann area 25. Likewise, the discharge portion of the catheter is also located in communication with Brodmann area 25. The electrical signal electrically stimulates Brodmann area 25 while the pump discharges the chemical agent into Brodmann area 25, to provide a combined, bi-modal therapeutic treatment for the eating disorder.

Triggered activation/deactivation. Preferably the desired stimulation, and resulting modulation, can be triggered by sensing of a predetermined event or condition or by manual activation from an external device, or from physician input or from patient input. If an above-described manual activation switch is included on the implantable controller, and should the physician determine that it is appropriate for the patient to have limited control over the device, the programming of the processor is adjusted to allow the signal generator to emit a predetermined stimulation signal upon detection by the controller of the requisite manual input from the patient.

Magnetic stimulation. As an alternative to surgical implantation of a DBS stimulator, an area of the brain such as the orbitofrontal cortex may instead be stimulated via transcranial magnetic stimulation. Thus, the stimulus can be electrical, chemical/drug, or magnetic, or a combination of any of those modes.

The above-described methods are believed to be useful to physicians in formulating appropriate therapeutic treatment of patients who suffer from serious uncontrolled binge eating/purging behavior. Bulimia is considered representative of other eating disorders that will also respond favorably to similar deep brain stimulation treatment.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. For instance, it should be understood that the various stimulation, sensing and activation modes, programmable features, and the like, that are described herein may be rearranged or employed in different combinations than those expressly exemplified. Many variations and modifications of the embodiments disclosed herein are possible and are within the scope of the invention. Accordingly, the scope of protection is not limited by the description set out above, but is only limited by the claims which follow, that scope including all equivalents of the subject matter of the claims. The disclosures of all patents, patent applications and publications cited herein are hereby incorporated herein by reference, to the extent that they provide exemplary, procedural or other details supplementary to those set forth herein.

What is claimed is:

1. A method of treating an individual suffering from an eating disorder, the method comprising:
    coupling a first stimulator to a predetermined stimulation site comprising a volume of neural tissue in an area of the individual's brain selected from the group consisting of insula, subcallosal area, cingulate, thalamus, prefrontal cerebral cortex, brain stem, cerebellum, and white matter tracts leading to an aforementioned area;
    coupling a second stimulator to a cranial nerve of the individual;
    applying a first predetermined stimulatory signal to said first stimulator; and
    applying a second predetermined stimulatory signal to said second stimulator, wherein said application of said first and second signals causes modulation of neuronal activity of said neural tissue to ameliorate the eating disorder.

2. The method of claim 1 wherein said second stimulatory signal comprises an acute stimulation component and a chronic stimulation component.

3. The method of claim 2 wherein said acute stimulation component comprises a higher intensity level of stimulation and shorter duration than said chronic stimulation component.

4. The method of claim 1 wherein said eating disorder is bulimia and said application of said first and second therapeutic stimulation signals alleviates binge eating and/or purging behavior in said individual.

5. The method of claim 1 wherein said application of said first and second therapeutic stimulation signals induces a feeling of satiety in said individual.

6. The method of claim 1 wherein said area comprises at least a portion of the insula or a white matter tract leading to a portion of the insula.

7. The method of claim 6 wherein said area comprises a portion of the insula chosen from the group consisting of the left and right anterior and posterior insula, and the claustrum, or a white matter tract leading to a portion of the insula.

8. The method of claim 1 wherein said area comprises at least a portion of a subcallosal area or a white matter tract leading to a portion of a subcallosal area.

9. The method of claim 1 wherein said area comprises at least a portion of the cingulate or a white matter tract leading to a portion of the cingulate.

10. The method of claim 9 wherein said area comprises at least a portion of a Brodmann area chosen from the group consisting of Brodmann area 24, Brodmann area 25 and Brodmann area 32.

11. The method of claim 1 wherein said area comprises at least a portion of the prefrontal cortex or a white matter tract leading to said portion of the prefrontal cortex.

12. The method of claim 11 wherein said area comprises at least a portion of a Brodmann area chosen from the group consisting of Brodmann area 8, Brodmann area 9, Brodmann area 10 and Brodmann area 11.

13. The method of claim 1 wherein said area comprises at least one nucleus in the thalamus or a white matter tract leading to a nucleus in the thalamus.

14. A method of treating an individual suffering from an eating disorder, the method comprising:
    providing a controller comprising a signal generator and processor in communication with a first electrode and a second electrode;
    coupling said first electrode to a cranial nerve of the individual;
    coupling said second electrode to an area of the individual's brain selected from the group consisting of insula, subcallosal area, cingulate, thalamus, hypothalamus, prefrontal cerebral cortex, brain stem, cerebellum, and white matter tracts leading from an aforementioned area;
    applying a predetermined electrical signal to said first electrode; and
    sensing electrical activity in said selected area of the brain by said second electrode;
    comparing the sensed electrical activity to a predetermined electrical state of said selected area, to provide comparison results; and
    determining from said comparison results whether said application of said predetermined electrical signal to said first electrode causes a modulation of electrical activity of said brain area, wherein said modulation of electrical activity corresponds to alleviation of a symptom of an eating disorder.

15. The method of claim 14 wherein said first electrical signal comprises adjustable electrical parameters, and said method further comprises adjusting at least one parameter of said first electrical signal based on said comparison results.

16. The method of claim 14 wherein said step of sensing electrical activity in said selected area of the brain by said second electrode comprises subdural sensing.

17. The method of claim 14 wherein said cranial nerve is selected from the group consisting of vagus, hypoglossal, trigeminal and accessory nerves.

18. A method of treating an individual suffering from an eating disorder, the method comprising:
   providing a controller comprising a signal generator and processor in communication with a first electrode and a second electrode;
   coupling said first electrode to a cranial nerve of the individual;
   coupling said second electrode to an area of the individual's brain selected from the group consisting of insula, subcallosal area, cingulate, thalamus, prefrontal cerebral cortex, brain stem, cerebellum, and white matter tract s leading to an aforementioned area;
   applying a predetermined electrical signal to said second electrode to modulate neuronal activity of said selected area of the brain;
   sensing electrical activity in said cranial nerve by said first electrode;
   comparing the sensed electrical activity to a predetermined electrical state of said nerve, to yield comparison results;
   determining from said comparison results whether said application of said predetermined electrical signal to said second electrode causes a modulation of electrical activity of said cranial nerve.

19. The method of claim 18 wherein said second electrical signal comprises adjustable electrical parameters, and said method further comprises adjusting at least one parameter of said second electrical signal based on said comparison results.

20. An adaptive brain stimulation process for treating a patient suffering from an eating disorder, the process comprising:
   (a) providing a system comprising at least one sensor for coupling with a status indicator site on the patient to sense a present state of at least a first brain region or set of brain regions; a first stimulating circuit for coupling at least said first brain region or set of brain regions by at least one stimulation electrode, to carry out stimulation according to a first set of stimulation parameters; a comparator adapted for coupling with said at least one sensor, said comparator adapted for receiving data related to the present state and comparing said present state data with reference state data, such that said comparing results in a positive outcome or a negative outcome; and at least one control circuit coupled with at least said first stimulating circuit and adapted for being adjusted according to the outcome of said comparing of said present and reference states, to control said stimulation parameters;
   (b) coupling said at least one sensor with said a status indicator site on the patient;
   (c) stimulating at least a first brain region or a first set of brain regions of the patient according to a first set of stimulation parameters;
   (d) sensing a present state of said patient to provide sensed data;
   (e) comparing said sensed data with reference state data to derive comparison results;
   (f) determining from said comparison results whether a change in the stimulation parameters is necessary;
   (g) if said change is necessary, determining what changes are to be made in said stimulation parameters;
   (h) changing said first set of stimulation parameters as determined in step (f); and
   (i) repeating steps (c)-(h) with the resulting changed stimulation parameters, until no further change is determined to be necessary in step (g), wherein no change is necessary when stimulation according to a changed set of stimulation parameters ameliorates a symptom of said eating disorder.

21. The process of claim 20 further comprising stimulating a second brain region or a second set of brain regions of the patient if the comparison results indicate that a response signal causes a therapeutic benefit.

22. The process of claim 21 wherein said step of stimulating a second brain region or a second set of brain regions causes a beneficial therapeutic effect.

23. The a process of claim 20 wherein step (d) comprises sensing neuronal activity of a peripheral cranial nerve.

24. The process of claim 20 wherein, in step (g), changing said stimulation parameters comprises providing a stimulation signal that stimulates selective parasympathetic afferents of the cranial nerves to activate at least one cranial nerve pathway chosen from the group consisting of the gustatory pathways, olfactory, pro-inflammatory or anti-inflammatory pathways, respiratory pathways, cardiac pathways, baroreceptor pathways, the somatosensory pathways, satiety pathways, and noradrenergic, serotoninergic, dopaminergic and cholinergic neurotranamitter pathways.

* * * * *